United States Patent [19]

Thayer et al.

[11] Patent Number: 4,725,658
[45] Date of Patent: Feb. 16, 1988

[54] NOVEL SILICONE-ESTER WAXES

[75] Inventors: Bianca K. Thayer, Saratoga Springs; Frank J. Traver, Troy, both of N.Y.

[73] Assignee: General Electric Company, Waterford, N.Y.

[21] Appl. No.: 926,848

[22] Filed: Nov. 3, 1986

Related U.S. Application Data

[63] Continuation of Ser. No. 775,468, Sep. 12, 1985, abandoned.

[51] Int. Cl.$^4$ .............................................. C08G 77/06
[52] U.S. Cl. ........................................ 528/15; 528/31; 528/26; 528/26.5; 556/437
[58] Field of Search ................. 528/26, 15, 31, 26.5; 556/437

[56] References Cited

U.S. PATENT DOCUMENTS 2,823,218  2/1958  Speier et al. ........................... 528/15
3,112,333  11/1963  Bailey .................................... 528/26
3,296,196  1/1967  Lamoreaux ........................... 528/26

Primary Examiner—Melvyn I. Marquis
Attorney, Agent, or Firm—Gary L. Loser; John W. Harbour

[57] ABSTRACT

There are provided novel silicone-ester waxes having the general unit formula

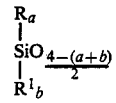

where R is hydrogen or an organic radical, R$^1$ is an ester-containing radical having at least 12 carbon atoms, a and b are independently selected integers from 0 to 3 inclusive, and the sum of a+b has an average value from about 1.0 to about 3.0, with the proviso that there is present at least one R$^1$ radical.

17 Claims, No Drawings

NOVEL SILICONE-ESTER WAXES

This application is a continuation of application Ser. No. 775,468, filed 9/12/85, now abandoned.

BACKGROUND OF THE INVENTION

The present invention relates to novel waxes and methods for making such waxes. More particularly, the present invention relates to novel silicone-ester waxes having at least one ester moiety comprised of at least about twelve carbon atoms.

Cosmetics manufacturers are continually attempting to provide improved personal products such as lipsticks, eye-shadows, bronzes, blushes, lotions, handcreams, and the like. A good lipstick, for example, must possess a certain maximum and minimum of thixotropy; i.e., it must soften enough to yield a smooth, even application with a minimum of pressure. The applied film should to some extent be impervious to the mild abrasion encountered during eating and drinking. Furthermore, the lipstick should be of such composition as to color only that portion of the lip to which it is applied, and should not bleed, streak or feather into the surrounding tissue of the mouth. Resistance to moisture and ease of application are also important properties as are a good "gloss" and "feel".

Heretofore it has been the general practice in the cosmetics art to utilize various natural waxes such as carnauba wax, candelilla wax, and the like to impart different characteristics such as hardness, thixotropy, melting point, and ease of application. Lanolin and various derivatives are often used for their emollient properties and for a degree of tackiness and drag. A highly refined grade of castor oil is used primarily to impart viscosity to the molded stick and, secondly, as a solvent for bromo derivatives of fluorescein which produce indelibility in the applied film.

It has now been found that certain novel silicone-ester waxes having at least one ester moiety of at least twelve carbon atoms can be used in place of many natural waxes to provide improved cosmetic formulations.

SUMMARY OF THE INVENTION

It is an object of the present invention to provide novel silicone-ester waxes useful in cosmetic and personal care formulations.

It is another object of the present invention to provide a method for making the novel silicone-ester waxes of the present invention.

In accordance with one aspect of the present invention there are provided novel silicone-ester waxes having at least one ester moiety of at least twelve carbon atoms. Preferably, the silicone-ester waxes have the general formula

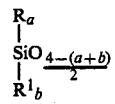

where R is hydrogen or an organic radical, $R^1$ is an ester-containing radical having at least 12 carbon atoms, a is an integer from 0 to 3 inclusive, b is an integer from 0 to 3 inclusive, and the sum of a+b has an average value of from about 1.0 to about 3.0, with the proviso that there is present at least one $R^1$ radical.

According to a method of the present invention, the novel silicone-ester waxes are prepared by reacting an ester having terminal olefinic unsaturation with an organohydrogenpolysiloxane in the presence of an effective amount of hydrosilation catalyst.

DESCRIPTION OF THE INVENTION

In its broadest aspect, the present invention provides novel silicone-ester waxes having at least one ester moiety of at least twelve carbon atoms. Preferably, the silicone ester waxes of the present invention have the general unit formula

where R is hydrogen or an organic radical; $R^1$ is an ester-containing radical having at least 12 carbon atoms; a is an integer from 0 to 3 inclusive; b is an integer from 0 to 3 inclusive, and the sum of a+b has an average value of from about 1.0 to about 3.0; with the proviso that there is present at least one $R^1$ radical. Preferably, the silicone-ester waxes of the present invention have a melting point of at least about 30° C. and, more preferably, have a melting point of from about 40° C. to about 90° C.

Those of ordinary skill in the art will appreciate that the siloxane chain can be substantially linear or resinous (e.g. highly branched). It is preferred that the siloxane be substantially linear. Of course, mixtures of linear and resinous polysiloxanes are also contemplated by the present invention.

The starting polysiloxanes utilized to make the silicone-ester waxes of formula I are preferably organohydrogenpolysiloxanes. The preferred organohydrogenpolysiloxanes are linear polymers of the general formula

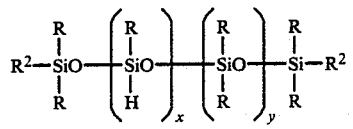

where R is an organic radical, $R^2$ is hydrogen or an organic radical, and x and y vary such that the polymer has a viscosity of from about 5 to 1000 centipoise at 25° C., with the proviso that if x equals zero $R^2$ is hydrogen. Such linear hydride polymers preferably have from about 10 to 100 mole percent Si-H containing siloxy units.

The preferred organohydrogenpolysiloxane resins comprise

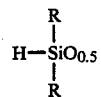

and $SiO_2$ units, where the sum of R and H to Si varies from 1.0 to 3.0. Such resins may also include a limited number of difunctional units.

These and other suitable organohydrogenpolysiloxanes are well known in the art, for example, as described in U.S. Pat. Nos. 3,344,111 and 3,436,366, both of which are incorporated by reference into the present disclosure.

The R radicals in the foregoing formulas can be any substituted or unsubstituted organic radicals, for example, alkyl radicals such as methyl, ethyl, propyl, hexyl, octyl, decyl, cyclohexyl, cycloheptyl, and the like; aryl radicals such as phenyl, tolyl, xylyl, naphthyl, and the like; aralkyl radicals such as phenylethyl, benzyl, and the like; or any of the foregoing wherein one or more hydrogen atoms is replaced with, for example, a halogen, cyano, amino, or the like. Most preferably, all of the R radicals are methyl or a mixture of methyl and phenyl.

The present invention is based on the discovery that silicone-ester waxes particularly useful in cosmetic formulations can be prepared from organohydrogenpolysiloxanes and alcohol esters of fatty acids having terminal olefinic unsaturation. Thus, $R^1$ of the above formula I, prior to reaction with the organohydrogenpolysiloxane, can be represented, for example, by the general formula

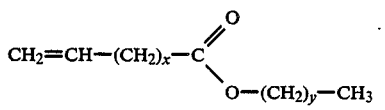

where x and y are independently selected integers equal to or greater than 4; and preferably are equal to or greater than 8. Such compounds can be prepared by reacting an alcohol with a carboxylic acid having terminal olefinic unsaturation. Thus, by way of illustration,

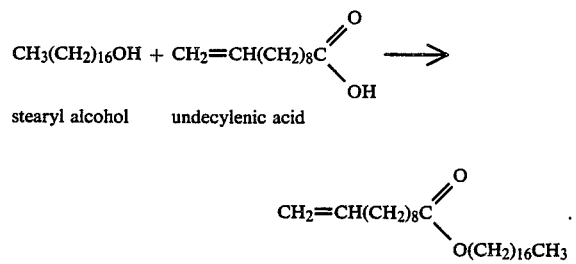

Alternatively, $R^1$ of formula I, prior to reaction with the organohydrogenpolysiloxane, can be prepared by reacting an alcohol having terminal olefinic unsaturation with a carboxylic acid. Thus, by way of illustration,

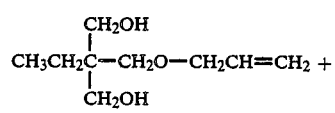

trimethylolpropane monoallylether

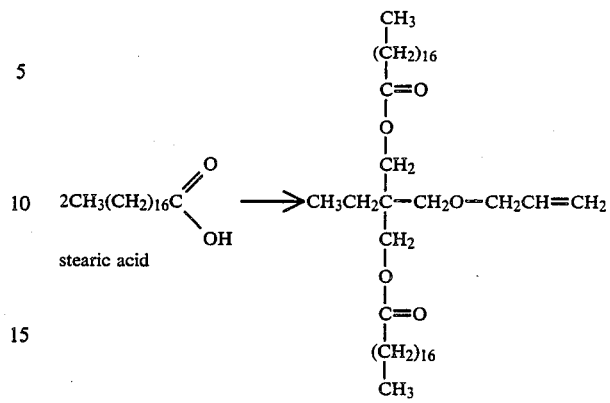

If only one ester moiety is desired, the artisan can substitute a mono-alcohol such as, for example, allyl alcohol or a homolog thereof.

Other variations will be obvious to those of ordinary skill in the art. However, it should be understood that $R^1$, prior to reaction with the organohydrogenpolysiloxane, must contain at least 12 carbon atoms and, preferably, at least 20 carbon atoms, so as to impart a waxy consistency to the composition of formula I, and must also contain terminal olefinic unsaturation.

The terminal olefinic unsaturation allows the organic ester (e.g. $R^1$) to be added to the organohydrogenpolysiloxane in the presence of a hydrosilation catalyst. Suitable hydrosilation catalysts are well known in the art, for example, platinum containing catalysts as described in U.S. Pat. Nos. 3,159,601; 3,159,662; 3,220,970; 3,516,946 and 3,814,730, all of which are incorporated by reference into the present disclosure. Other suitable hydrosilation catalysts can be based on the metals rhodium, ruthenium, palladium, osmium, irridium and platinum. Generally, the olefinically unsaturated ester can be added to the organohydrogenpolysiloxane in the presence of from about 10 to about 500 ppm of catalyst, based on the metal.

For purposes of illustration, the foregoing organic esters can be added to an organohydrogenpolysiloxane to obtain the novel silicone-esters of the present invention as follows:

$$CH_2=CH(CH_2)_8C{\overset{O}{\underset{O(CH_2)_{16}CH_3}{\diagdown}}} + \underset{R}{\overset{R}{HSiO}}\diagup\!\!\!\diagdown\!\!\diagup \xrightarrow{Pt}$$

$$\diagup\!\!\!\diagdown\!\!\diagup OSi\underset{R}{\overset{R}{|}}-CH_2CH_2(CH_2)_8-C{\overset{O}{\underset{O(CH_2)_{16}CH_3}{\diagdown}}};$$

and

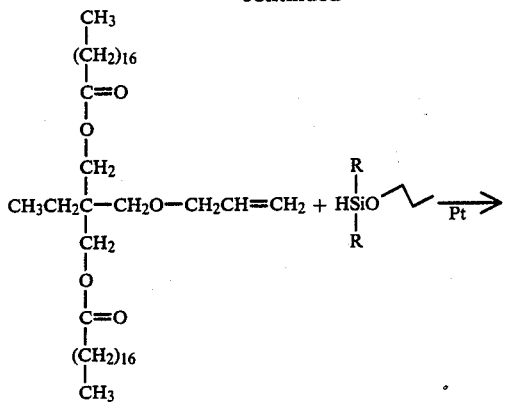

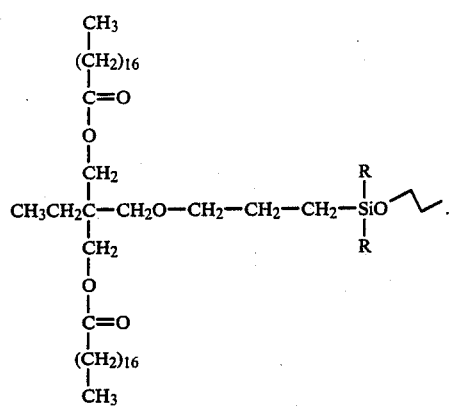

The artisan will appreciate that the number of ester moieties required to impart a waxlike consistency to the final product will vary depending upon the number of siloxy units, whether the polysiloxane is fluid or resinous, and the number of carbon atoms in the ester moiety. Based on the foregoing description, the skilled artisan will be able to select suitable reactants for preparing the novel silicone-ester waxes of the present invention without undue experimentation.

It is also contemplated that the silicone-ester waxes of the present invention can contain long chain alkyl radicals to increase the melting point of the wax as well as to improve its consistency. Such long chain alkyl radicals are at least about 16 carbon atoms in length and, preferably, are from about 24 to about 36 carbon atoms in length. Terminal olefinic unsaturation should be present so that the long chain alkyl can be added to the organohydrogenpolysiloxane via a hydrosilation reaction; i.e.

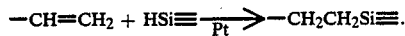

In order to better enable the artisan to practice the present invention, the following examples are provided by way of illustration and not by way of limitation. All parts and percentages are by weight unless otherwise noted.

EXAMPLES

Example 1

To a one liter round bottom 3-neck flask equipped with stirrer, thermometer, and reflux head, there was added 87 grams trimethylolpropane monoallylether (TMPMAE), 284 grams stearic acid, 1 gram p-toluene sulfonic acid catalyst, and 400 grams toluene as solvent. The mixture was heated to 120° C. (reflux) and held for six hours, during which time water was removed from the toluene/water azeotrope and the esterification driven to completion. Infrared spectroscopy indicated deletion of the organic acid peak and the presence of the ester. Once the reaction was complete the p-toluene sulfonic acid catalyst was neutralized with sodium bicarbonate.

To the thus prepared ester there was added an effective amount of platinum-containing catalyst prepared in accordance with U.S. Pat. No. 3,814,730. The mixture was warmed to 105° C. at which time a hydrogen-terminated polydiorganosiloxane was added. An exotherm was noted and the rate of addition was rather rapid. After an equivalent amount of organohydrogenpolysiloxane was added to the reaction vessel, the solution was heated at reflux until all of the Si-H was consumed (based on IR analysis). The resultant silicone-ester wax was stripped under vacuum to remove toluene and thereafter filtered while hot through Celite #545 to improve its appearance. The wax had a melting point of 30° C. and can be represented by the formula

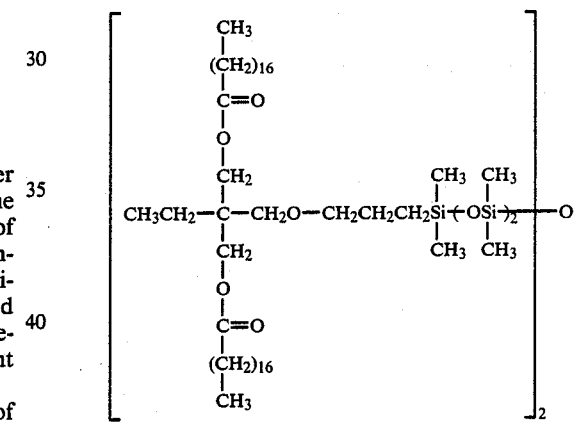

Example 2

To a one liter 3-neck flask equipped as in Example 1 there was added 116 grams undecylenic acid, 176 grams stearyl alcohol, 300 grams toluene as solvent, and 0.5 gram p-toluene sulfonic acid catalyst. The solution was heated to 120° C. and the water removed from the toluene/water azeotrope. After about 6 hours the IR scan of the reaction mass indicated conversion of the organic acid to the ester. The p-toluene sulfonic acid was neutralized with sodium bicarbonate. An effective amount of the catalyst utilized in Example 1 was added to the vessel and warmed to 105° C. Then 37.7 grams of DF 1040 fluid (available from General Electric Company) was added and the vessel heated at 120° C. for an hour after the methylhydrogen silicone fluid (DF 1040) addition. At this time the olefin-ester addition to the organohydrogenpolysiloxane was complete, and the resultant wax was stripped under vacuum to remove toluene. The hot wax was then filtered through Celite #545. The thus obtained wax had a melting point of 43°–45° C. and can be represented by the formula

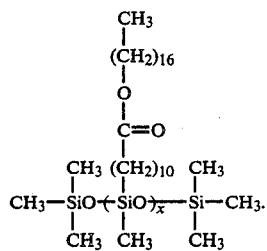

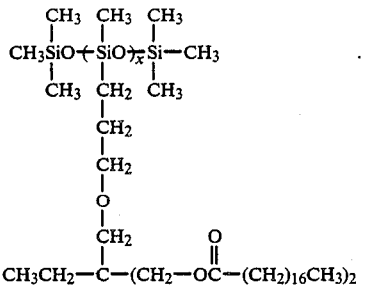

Example 3

There was prepared a mixed mono/di ester of trimethylolpropane monoallyl ether (87 grams) and stearic acid (213 grams) using the procedure of Example 1. The ester was formed in the presence of 231 grams $C_{30-34}$ alpha-olefin available from Gulf Chemicals. Once the ester was formed, the p-toluene sulfonic acid catalyst was neutralized and an effective amount of hydrosilation catalyst added. The mixture was heated to 105° C., and 1 mol of MeHSiO (SS 4300c available from General Electric Company) was added to produce a methylalkyl/methylester silicone wax. An additional 25 grams of alpha-olefin was required to eliminate all of the Si-H peaks on the IR scan. The mixed ester/alkyl wax had a melting point of 52°-55° C. and can be represented by the formula

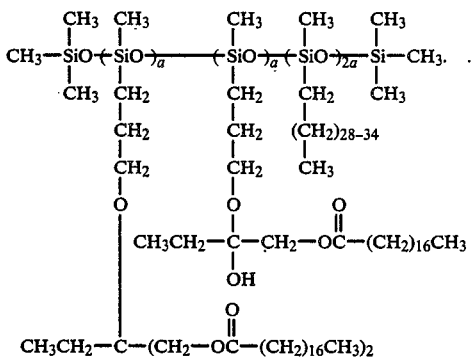

Example 4

There was prepared the distearic acid ester of trimethylolpropane monoallylether from 87 grams trimethylolpropane monoallylether and 284 grams stearic acid following the procedure of Example 1. Thirty grams of methylhydrogen silicone fluid (DF 1040) was added in the presence of an effective amount of hydrosilation catalyst to prepare a silicone-ester wax having a melting point of 33°-34° C. and which can be represented by the formula The foregoing silicone-ester waxes can be used in stick formulation cosmetics, such as lipstick, bronzes, blushes and eyeshadows, in both conventional and fully silicone systems.

We claim:

1. A silicone-ester wax comprising moieties of the general unit formula:

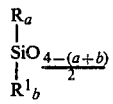

where R is hydrogen or an organic radical; $R^1$ is an ester-containing radical having at least 12 carbon atoms; a is an integer from 0 to 3 inclusive, b is an integer from 0 to 3 inclusive; the sum of a+b has an average value to render the siloxane chain substantially linear; there is present at least one $R^1$ radical on said wax; and said wax has a melting point between about 30° C. and 90° C.

2. A composition as in claim 1, wherein $R^1$ has at least 20 carbon atoms.

3. A composition as in claim 1, wherein the silicone-ester wax has a melting point of from about 40° C. to about 90° C.

4. A composition as in claim 1, wherein $R^1$ is prepared from a carboxylic acid having terminal olefinic unsaturation and an alcohol.

5. A composition as in claim 4, wherein $R^1$ has the general formula

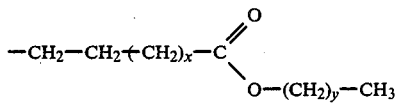

where x and y are independently selected integers equal to or greater than 4.

6. A composition as in claim 5, wherein x and y are independently selected integers equal to or greater than 8.

7. A composition as in claim 6, wherein the carboxylic acid is undecylenic acid and the alcohol is stearyl alcohol.

8. A composition as in claim 1, wherein $R^1$ is prepared from an alcohol having terminal olefinic unsaturation and a carboxylic acid.

9. A composition as in claim 8, wherein $R^1$ has at least 16 carbon atoms.

10. A composition as in claim 9, wherein $R^1$ is prepared from trimethylolpropane monoallylether and stearic acid.

11. A silicone-ester wax composition prepared by reacting an organic ester of at least 12 carbon atoms and having terminal olefinic unsaturation with a linear organohydrogenpolysiloxane in the presence of an effective amount of hydrosilation catalyst wherein said silicone ester wax has a melting point between about 30° C. and 90° C.

12. A composition as in claim 11, wherein the organic ester is the reaction product of an alcohol and a carboxylic acid having terminal unsaturation.

13. A composition as in claim 11, wherein the organic ester is the reaction product of an alcohol having terminal olefinic unsaturation and a carboxylic acid.

14. A composition as in claim 13, wherein the alcohol having terminal olefinic unsaturation is allyl alcohol.

15. A composition as in claim 13, wherein the alcohol having terminal olefinic unsaturation is trimethylolpropane monoallylether.

16. A composition as in claim 11, wherein the organohydrogenpolysiloxane is a fluid.

17. A composition as in claim 11, wherein there is further reacted a long chain alkyl radical having terminal olefinic unsaturation.

* * * * *